United States Patent [19]

Renzel

[11] Patent Number: 4,655,084

[45] Date of Patent: Apr. 7, 1987

[54] ULTRASONIC TEST INSTRUMENT

[75] Inventor: Peter Renzel, Düren, Fed. Rep. of Germany

[73] Assignee: Krautkramer-Branson, Inc., Lewistown, Pa.

[21] Appl. No.: 858,105

[22] Filed: May 1, 1986

[30] Foreign Application Priority Data

Jun. 3, 1985 [DE] Fed. Rep. of Germany ....... 3519797

[51] Int. Cl.$^4$ .......................................... G01N 29/04
[52] U.S. Cl. ...................................... 73/611; 73/598; 73/600; 73/612
[58] Field of Search ................. 73/611, 612, 598, 600, 73/614, 597, 599

[56] References Cited

U.S. PATENT DOCUMENTS

| | | | |
|---|---|---|---|
| 3,872,715 | 3/1975 | Pittaro | 73/611 |
| 3,914,986 | 10/1975 | Ota et al. | 73/611 |
| 4,088,029 | 5/1978 | Yamamoto et al. | 73/612 |
| 4,364,114 | 12/1982 | Renzel et al. | 73/597 |
| 4,432,235 | 2/1984 | Renzel et al. | 73/611 |
| 4,492,118 | 1/1985 | Bathmann | 73/612 |
| 4,513,621 | 4/1985 | Renzel et al. | 73/611 |

Primary Examiner—Anthony V. Ciarlante
Attorney, Agent, or Firm—Philip J. Feig

[57] ABSTRACT

The invention relates to an ultrasonic test instrument for the nondestructive testing of materials. The instrument includes a transit time measuring circuit and an amplitude and time gate circuit. According to the invention, to measure the amplitudes and the corresponding transit times of a number of echo signals falling within a predetermined measurement range, the output of the amplitude and time gate circuit is connected to the input of a presettable counter which outputs a signal whenever the number of counted pulses is equal to the preset value of the counter. The counter output is connected to the transit time measuring circuit and by way of a second time gate circuit to the amplitude measuring circuit so that amplitude evaluation is carried out only during the time interval defined by the second time gate circuit.

2 Claims, 8 Drawing Figures

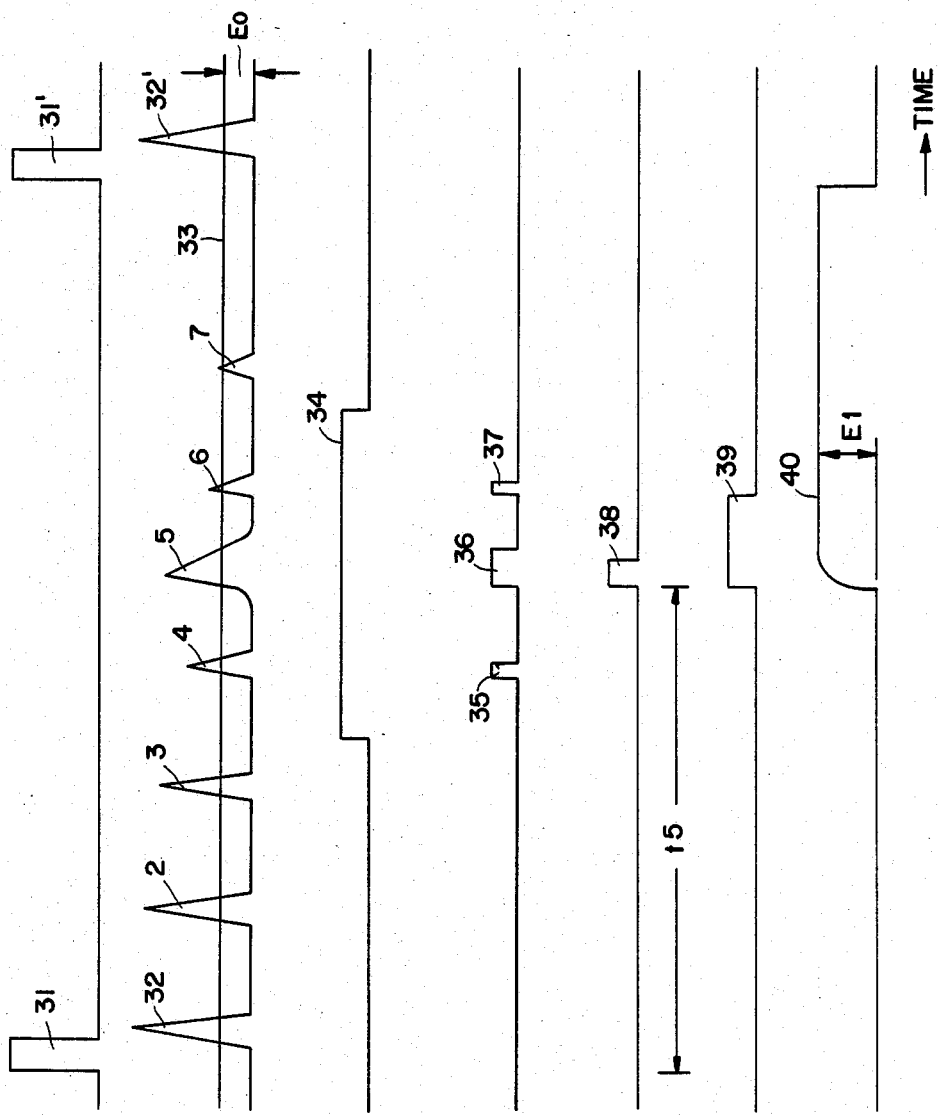

ULTRASONIC TEST INSTRUMENT

BRIEF SUMMARY OF THE INVENTION

This invention relates to an ultrasonic test instrument for the nondestructive testing of materials, the instrument having a transmitter which produces ultrasonic transmit signals at predetermined time intervals and a receiver to sense the amplitudes and the transit times associated therewith of a number of ultrasonic echo signals appearing during a predetermined measurement range. The echo signals are supplied to an amplitude and a first time gate circuit arrangement and then to a transit time and an amplitude measuring circuit for evaluating during the predetermined time interval only one echo signal at a time with respect to amplitude and transit time.

Instruments of this kind are known, see for instance, of Renzel et al U.S. Pat. Nos. 4,364,114 and 4,432,235. However, a disadvantage of these known instruments is that when a number of echo signals appear in the predetermined measurement range, the operator must adjust such range manually in a manner that only a single echo signal falls into the range per measurement. Accordingly, the predetermined measurement range is usually represented on the display screen of the apparatus as a gate bar which is moved delay-wise and width-wise relative to the echo to be evaluated until such bar covers only such echo.

Consequently, in automatic systems where manual adjustment of this type is not possible, the problem arises when a number of echo signals fall into the predetermined measurement range that the transit time measurement circuit can evaluate only the transit time of the first occurring echo signal, whereas the amplitude-measuring means evaluates whichever is the peak echo signal amplitude present in such range. However, the echo signal amplitude thus evaluated is not always associated with the first occurring echo signal.

It is an object of this invention so to provide a test instrument of the kind stated above having circuit means for replacing the manual adjustment of the gate bar in regard to the amplitude and transit time values of echo signals.

Another object of this invention is the provision of a circuit for automatically evaluating the amplitude and transit time values of echo signals occurring during a predetermined measurement range.

Still other objects of this invention will become apparent from the following description when read in conjunction with the accompanying drawings.

BRIEF DESCRIPTION OF THE DRAWING

FIG. 4 is a timing diagram for describing the operation of the circuit shown in FIG. 3;

DETAILED DESCRIPTION OF THE INVENTION

Figure 1:
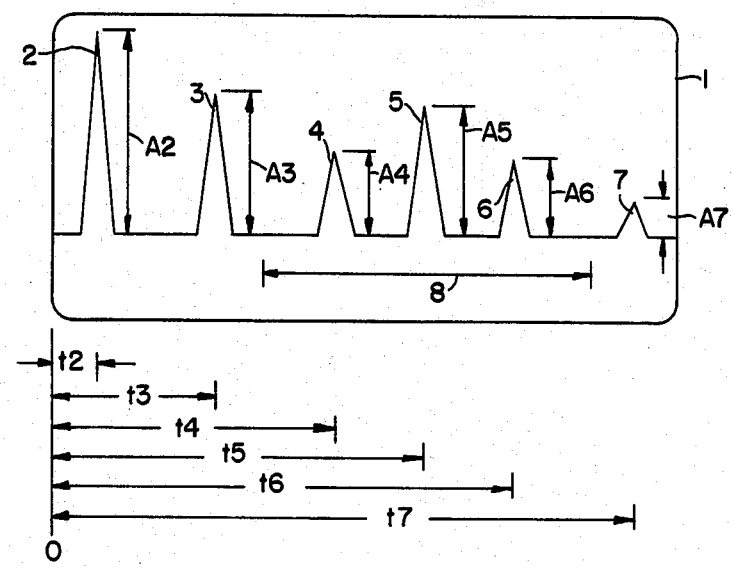
FIG. 1 is a view of the cathode ray tube screen of the ultrasonic test instrument for illustrating the present invention.
Figure 2:
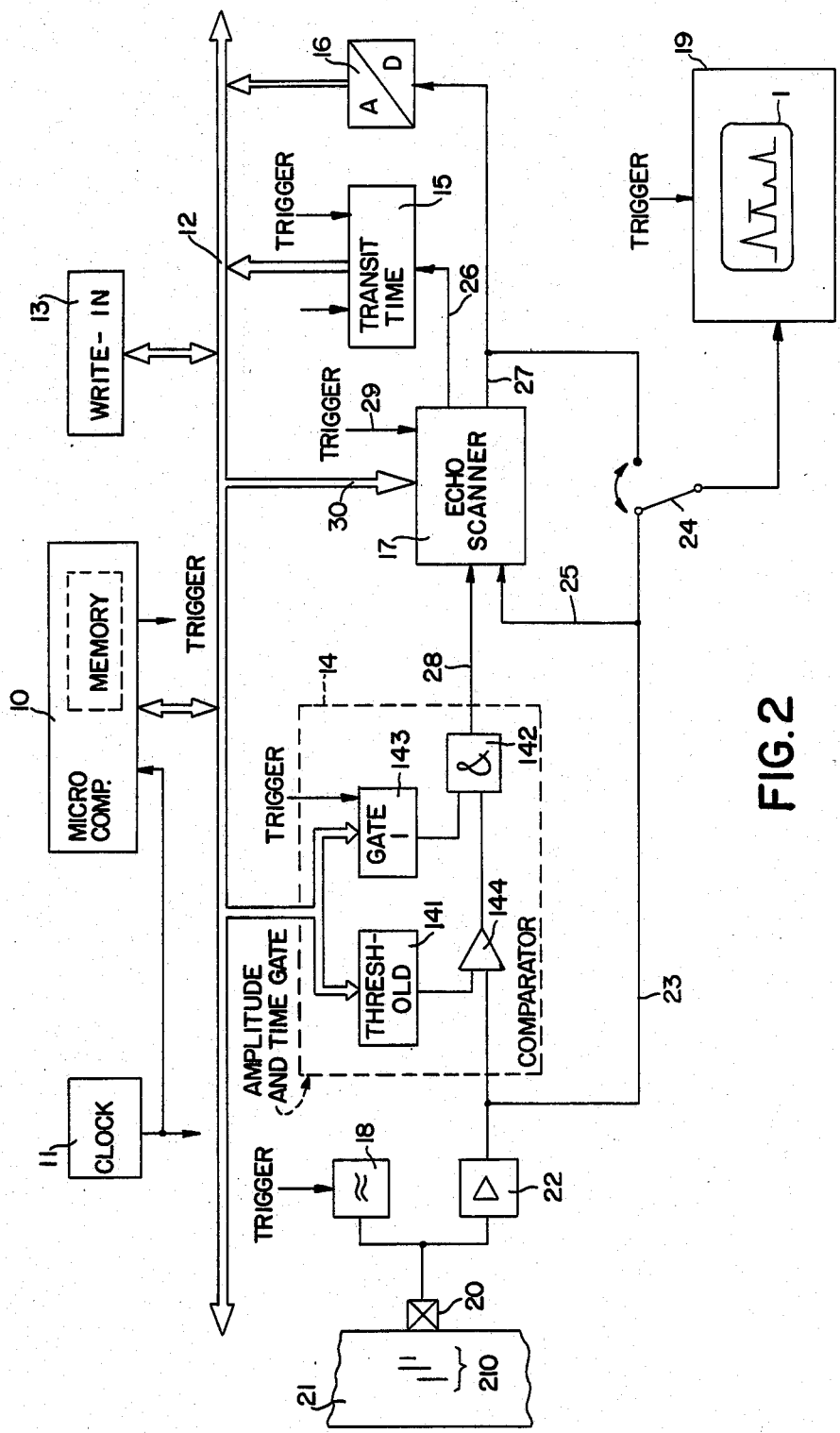
FIG. 2 is a schematic circuit diagram showing a microcomputer-controlled ultrasonic test instrument having an echo signal scanner according to the present invention.

The problem which the invention seeks to solve is illustrated in FIG. 1 when using an ultrasonic test instrument as shown in FIG. 2. There can be seen in FIG. 1 a display screen 1 of the ultrasonic test instrument and echo signals 2 to 7 displayed on the screen. An arrow 8 indicates the predetermined measurement range. The echo signals 2 to 7 have respective amplitudes A2 to A7 and the echo signals have corresponding transit times t2 to t7. The ultrasonic test instrument is required to measure the echo signal amplitudes A4, A5, A6 and the corresponding echo signal transit times t4, t5, t6 falling within the range 8. Specifically, the test instrument, according to the invention, is intended to be used for evaluating, upon selection, the amplitudes and transit times of individual echo signals, for example, the echo signal 6 falling within the range 8.

The embodiment of the invention shown in FIG. 2 will be described in greater detail hereinafter.

A microcomputer 10 and a clock 11 are provided for timing the microcomputer. By way of a bus 12 the microcomputer 10 is connected to an input unit 13, such as a keyboard, an amplitude and time gate unit 14, a transit time measuring circuit 15, an A/D converter 16 and an echo signal scanner 17. The microcomputer 10 also generates trigger signals for triggering the pulse generator 18 and the display device 19.

Coupled in circuit with the generator 18 is an ultrasonic test probe 20 which is acoustically coupled to a workpiece 21 to be tested. A receiving amplifier 22 is also coupled to the probe 20 and is followed, with the interconnection of the amplitude and time gate unit 14 and of the echo scanner 17 according to the invention, by a transit time measuring circuit 15 and an A/D converter 16.

The output of the receiver amplifier 22 is connected by a conductor 23 and a switch 24 to the display device 19 and by a conductor 25 to the echo scanner 17.

Since the circuitry shown in FIG. 2 is basically known from U.S. Pat. No. 4,364,114, except for the echo scanner 17, reference will be made hereinafter to the operation of this circuitry only to the extent necessary to explain the operation of the scanner 17 provided by the present invention.

Whenever the microcomputer 10 supplies a trigger signal to the pulse generator 18, the generator 18 generates a corresponding electrical transmit signal which is supplied to the probe 20. The ultrasonic search signal generated thereby enters the workpiece 21 to be tested and is reflected by defects 210 and by the workpiece rear wall. The reflected echo signals return to the probe 20, are converted into corresponding electrical signals and are supplied via receiver amplifier 22 to the amplitude and time gate circuit 14 and by conductor 23 and switch 24 to the display device 19.

In the amplitude and time gate circuit 14 the echo signal amplitudes are first evaluated in an amplitude gate comprising a comparator 144 and a threshold generator 141. The comparator 144 provides output signals only when the received ultrasonic echo signals exceed the threshold value produced by the threshold generator 141.

The signals at the comparator output then are fed to a time gate which determines the predetermined measurement range 8 and which is embodied by an AND gate 142 and a gate circuit 143, so that a signal appears at the output of the AND gate 142 and therefore at the output of the unit 14 only when the output signals of the amplitude gate coincide in time with the gating signal produced by the gate circuit 143.

The output signals provided by the unit 14 are fed by way of the echo scanner 17 and conductor 26 to the transit time measuring circuit 15. The latter circuit basically comprises a counter (not shown) which is started responsive to the trigger signal produced by the microcomputer 10 and which is stopped by the signal from the output of the echo scanner 17. The corresponding accumulated count is therefore a measure of the transit time of the particular echo signal.

Moreover, by means of the echo scanner 17, the particular echo signal amplitude values which are associated with the transit time value are evaluated and are supplied by means of conductor 27 to the A/D converter 16 and then by means of the bus 12 to the microcomputer 10. Using the switch 24, these amplitude values can also be supplied to the display device 19 and shown on the cathode ray tube screen 1.

Figure 3:
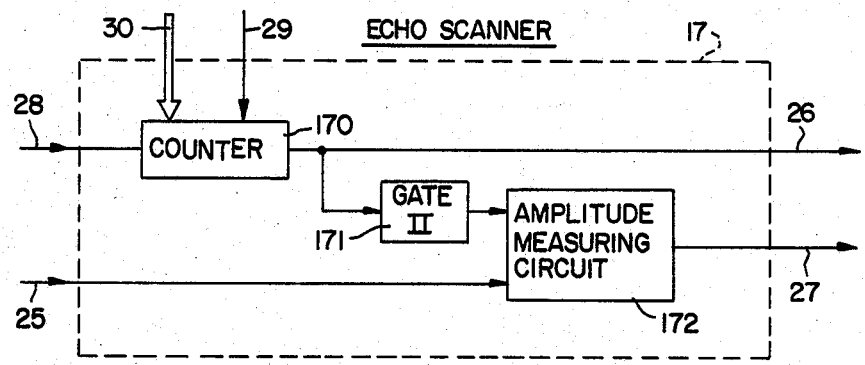
FIG. 3 is a schematic circuit diagram showing a first embodiment of an echo scanner according to the invention.

FIG. 3 shows an embodiment of the echo scanner 17 according to the invention. The scanner comprises a pre-settable counter 170 followed by a gate circuit 171 connected to the input of a known amplitude measuring circuit 172. The operation of the scanner 17 will be described in greater detail hereinafter with reference to the timing diagrams shown in FIGS. 4(a) to 4(g).

FIG. 4(a) shows trigger signals 31, 31' which arrive from the microcomputer 10 by way of the conductor 29 and which reset the counter 170 to the value preset by means of the bus 30 (initial state). It will be assumed, in the present example, that the value "two" has been preset. Consequently, when the second signal reaches the counter 170, by way of the conductor 28, the counter provides an output signal to the conductor 26.

FIG. 4(b) shows transmit signal pulses 32 and 32', and the echo signal pulses 2 to 7 (see also FIG. 1) and a threshold voltage 33 which is produced by the threshold generator 141 (FIG. 2) and which has a value Eo.

FIG. 4(c) shows the gate signal 34 produced by the gate circuit 143 and determining the predetermined measurement range.

Signals 35 to 37 shown in FIG. 4(d) therefore appear at the output of the amplitude and time gate circuit 14 (FIG. 2) and are fed by way of the conductor 28 to the counter 170 (FIG. 3) of the echo scanner 17. The counter responds to the arrival of the second signal 36 and causes an output signal 38 shown in FIG. 4(e). The signal 38 is operative to stop the transit time measuring circuit 15 (FIG. 2) and to start the gate circuit 171 (FIG. 3) which outputs a signal 39 shown in FIG. 4(f).

The gate circuit 171 is constructed to cause the width of the signals 39 to be substantially equal to the maximum width of one echo signal. The gate signal 39 is fed to the known amplitude measuring circuit 172. For the duration of the signal 39 the amplitude measuring circuit 172 measures the maximum amplitude E1 of the echo signal arriving by way of the conductor 25 at the other input of the circuit 172. FIG. 4(g) shows the shape of the voltage signal 40 appearing at the output of the amplitude measuring circuit 172. The voltage E1 is digitized by means of the A/D converter 16 and transmitted to the microcomputer 10. The voltage E1 can be applied by way of the switch 24 to the display device 19 so that the operator of the test instrument can read off directly not only the echo signals but also the corresponding peak values.

When with the next trigger signal 31' (FIG. 4(a)) the microcomputer 10 alters the presetting of the conductor 30 from "two" to "three", in the next time interval the amplitude and the transit time of the echo signal 6 are evaluated correspondingly. The circuit described enables the amplitude and transit time of n echo signals to be measured, displayed and/or stored automatically in n time intervals. This process can, for example, be interrupted automatically if in the n+1th time interval no signal appears at the output of the counter 170.

Figure 5:
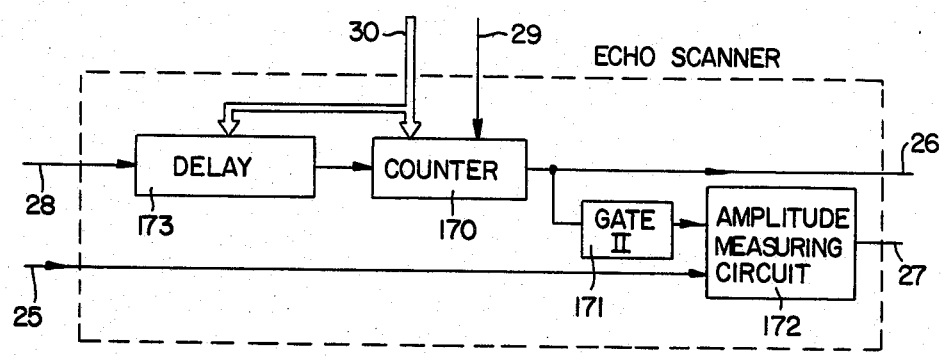
FIG. 5 is a schematic circuit diagram showing a second embodiment of an echo scanner according to the invention.

FIG. 5 shows an echo scanner which is a modification of that shown in FIG. 3. In addition to the counter 170, gate circuit 171 and amplitude measuring circuit 172, there is provided a delay circuit 173 which precedes the counter 170. The purpose of the delay circuit 173 is to compensate for any individual oscillations occurring within an echo signal so that only one signal per echo is produced which can be unambiguously registered in the counter.

The operation of the delay stage 173 can be visualized with reference to FIG. 6. Echo signals 42, 43 shown in FIG. 6(a) have additional individual oscillations, with the result that the amplitude and time gate circuit 14 (FIG. 2) and FIG. 6(c) would provide consecutively six signals instead of four signals during the predetermined measurement range 8. The delay stage 173 is so designed that an individual signal of duration T1 reaching the input of the delay stage 173 produces a corresponding output signal of duration T2. Should a second signal separated by the time interval T3 from the first signal arrive during the period T2, the delay stage 173 outputs only a single signal having the duration T2+T3. FIG. 6(d) shows the corresponding signals.

Figure 6A:
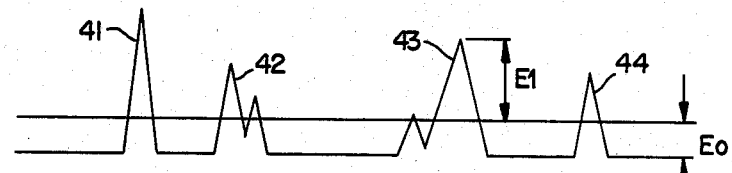
FIG. 6 is a timing diagram for describing the operation of the circuit shown in FIG. 5.
Figure 6B:
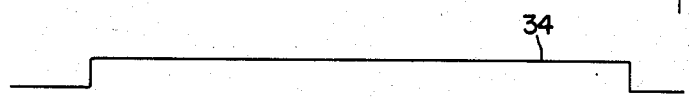
Figure 6C:
Figure 6D:
Figure 6E:
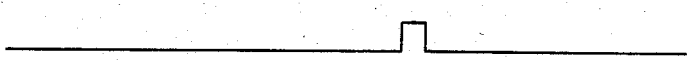
Figure 6F:
Figure 6G:

FIGS. 6(e), 6(f) and 6(g) correspond to FIGS. 4(e), 4(f) and 4(g), the counter 70 being preset in the present case to the value "three" so that the amplitude and the transit time of the echo signal 43 are evaluated.

Figure 7:
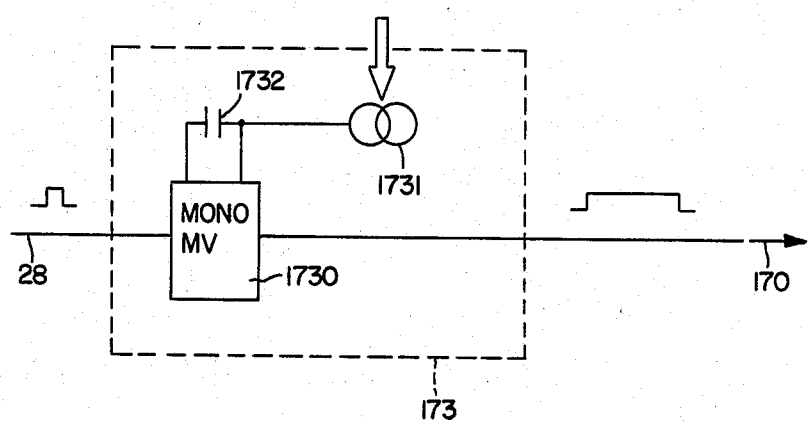
FIG. 7 is a schematic block diagram of a delay stage used in the embodiment of FIG. 5.

FIG. 7 shows an embodiment of the delay stage 173. It mainly comprises a commercially available retriggerable monostable multivibrator 1730 (e.g. type 74 LS 123) connected to a programmable current supply 1731. The programmable current supply determines in association with a capacitor 1732 of the monostable multivibrator the holding time thereof which is adjusted in dependence upon the required echo signal duration.

Figure 8:
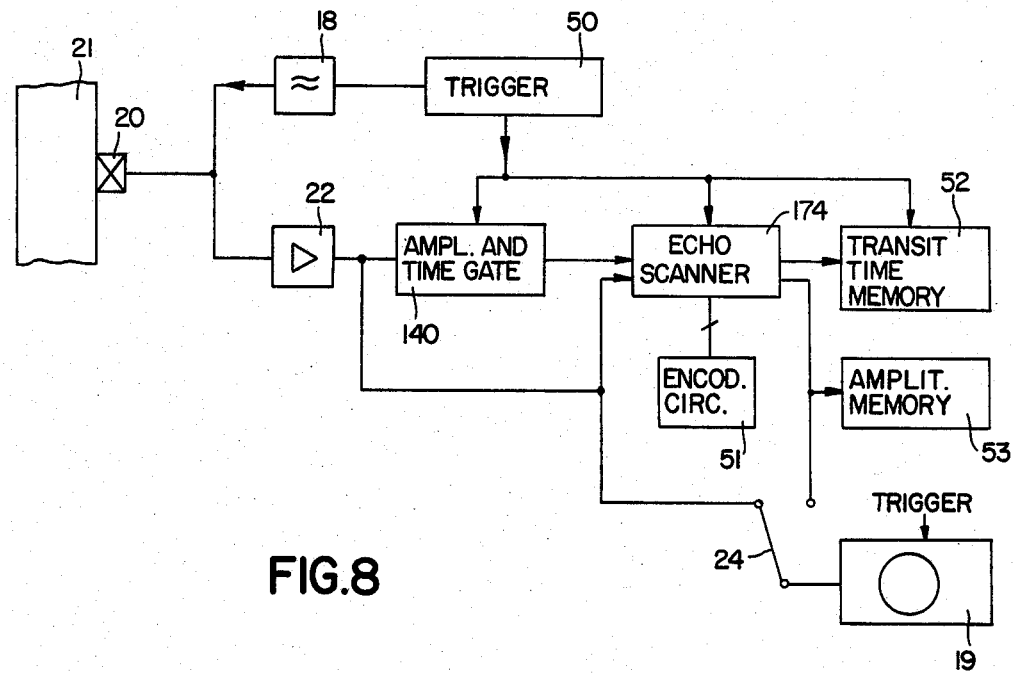
FIG. 8 is a diagram showing a conventional ultrasonic test instrument in which an echo scanner according to the invention is used.

The echo scanner according to the invention is of course not limited to microcomputer controlled ultrasonic instruments. FIG. 8 shows the embodiment of an ultrasonic instrument without a microcomputer, the various circuit units being triggered by way of a trigger stage 50 which precedes the pulse generator 18. The generator outputs corresponding signals at a constant pulse repetition rate. The echo scanner circuit arrangement 174 corresponds to the embodiments shown in FIGS. 3 and 5. In this case the counter 170 is preset by means of an encoding switch 51. The transit time and amplitude values are stored in corresponding memories 52 and 53.

While there have been described and illustrated a preferred embodiment of this invention and several modifications thereof, it will be apparent to those skilled in the art that various further changes and modifications can be made without departing from the broad principle of this invention which shall be limited only by the scope of the appended claims.

What is claimed is:

1. An ultrasonic test instrument for the nondestructive testing of workpieces including a pulse generator for producing ultrasonic transmit signals at predetermined time intervals and a receiver for receiving ultrasonic echo signals corresponding to the transmit signals and evaluating the amplitudes and the transit times of the ultrasonic echo signals appearing during an expected measurement range, the latter signals being supplied to an amplitude and a first time gate circuit and to a transit time measuring circuit and an amplitude measuring circuit for causing only one echo signal at a time to have its amplitude and transit time evaluated between the predetermined time intervals, the improvement comprising:

a presettable counter coupled for receiving the output signal from said amplitude and time gate circuit and providing an output signal whenever the number of pulses received at the input of said counter is equal to the preset value of said counter;

said output signal from said counter being coupled to said transit time measuring circuit as well as by means of a second time gate circuit to said amplitude measuring circuit, whereby to cause said amplitude measuring circuit to evaluate an echo signal only during the time interval defined by said second time gate circuit.

2. An ultrasonic test instrument as set forth in claim 1 and a delay circuit coupled in series with said presettable counter for combining a number of signals received consecutively within a predetermined time interval from said amplitude and time gate circuit into a single signal.

* * * * *